United States Patent [19]
Bartlett

[11] Patent Number: 4,580,097
[45] Date of Patent: Apr. 1, 1986

[54] ELECTRONIC PROXIMITY SENSOR WHICH IS RESPONSIVE TO INDUCED RESISTANCE

[75] Inventor: Peter G. Bartlett, Davenport, Iowa

[73] Assignee: Automation Systems, Inc., Eldridge, Iowa

[21] Appl. No.: 595,243

[22] Filed: May 23, 1984

Related U.S. Application Data

[63] Continuation of Ser. No. 311,508, Oct. 15, 1981, abandoned, which is a continuation of Ser. No. 37,527, May 9, 1979, abandoned.

[51] Int. Cl.$^4$ .................. G01N 27/12; G01R 33/12; G01B 7/14; G08B 19/00
[52] U.S. Cl. .................................. 324/226; 324/207; 324/234; 331/65
[58] Field of Search ............... 324/207, 208, 225, 226, 324/236–243, 227, 234; 331/65, 117 R; 340/941

[56] References Cited

U.S. PATENT DOCUMENTS

| | | | |
|---|---|---|---|
| 3,319,160 | 5/1967 | Wood et al. | 324/226 |
| 3,453,532 | 7/1969 | Gardiner et al. | 324/235 |
| 3,609,580 | 9/1971 | Thompson et al. | 324/236 |
| 3,688,187 | 8/1972 | Loos | 324/234 |
| 3,743,853 | 7/1973 | Dittman et al. | 331/65 |
| 4,042,876 | 8/1977 | Visioli, Jr. | 324/207 |

Primary Examiner—Ernest F. Karlsen
Assistant Examiner—Walter E. Snow
Attorney, Agent, or Firm—Woodard, Weikart, Emhardt & Naughton

[57] ABSTRACT

An improved electronic proximity sensor and crack detector that is primarily responsive to the induced resistance in a coil; including an LC resonating circuit that utilizes constant current and a DC power source. By sensing changes in the induced resistance, the invention detects various conditions of parts present and probe fault and can detect a crack in a rotating metal object that is in proximity with the probe. This is accomplished by sensing changes in the induced resistance that occur at the same frequency at which the metal object is rotating.

17 Claims, 5 Drawing Figures

ELECTRONIC PROXIMITY SENSOR WHICH IS RESPONSIVE TO INDUCED RESISTANCE

This application is a continuation of application Ser. No. 311,508, filed 10/15/81 now abandoned which is a continuation of app. Ser. No. 37,527, filed 5/9/79, now abandoned.

BACKGROUND

1. Field of the Invention

The field of the invention is proximity sensors. More specifically the field of the invention is those sensors which utilize electronic oscillation circuitry.

2. Brief Description of the Prior Art

Various proximity sensors utilizing electronic oscillation circuitry appear in the prior art. Hardin U.S. Pat. No. 3,473,110 discloses one such circuit utilizing an LC resonator. The presence of an electrically conducting object in proximity with the probe of this invention causes a decrease in the gain of the oscillation. This decrease in gain is detected by a bi-stable demodulator. In Buck U.S. Pat. No. 3,747,012 the decrease in amplitude of oscillation triggers a thyristor which changes the current flow of the circuit. This causes a signal to be given indicating that an electrically conducting object is in proximity with the probe. In Scruggs U.S. Pat. No. 3,919,629 the oscillation of the resonating circuit ceases because of increased inductance of the probe that is the result of the existence of a metal object in proximity with the probe. Scruggs uses a power switching network that includes a diode bridge and a thyristor.

Prior art circuits generally are not substantially responsive to the induced resistance of the metal object being detected. The circuits typically respond to a change in frequency when a metal object comes into proximity with the probe. The circuits do not utilize a constant current when in operation, tending to make detection of output sensor signals less stable, less uniform in response, or more complicated. Typically the detection circuit in the prior art is not sophisticated, not providing for probe fault indication signals, and not providing for crack detection.

SUMMARY

The present invention utilizes a simple LC resonating circuit that is primarily responsive to the induced resistance of a probe and is relatively insensitive to changes in induced reactance. In the sensor circuit, an LC resonator is alternately controlled by two switching transistors, which are in turn controlled by the LC resonator through an inductive coupling. One aspect of the preferred circuit is a constant current arrangement between two fixed voltages. The result of this basic configuration is an oscillator that is primarily responsive to changes in induced resistance in the LC circuit and is relatively insensitive to changes in induced reactance.

The LC resonating circuit of the invention utilizes a constant current and a D.C. power source. It is inherent with the circuit of the preferred embodiment, that the transistor T1 providing the constant current source to the LC resonating circuit is biased so that it does not saturate when it is conducting. Without saturation, the effects of external reactances and resistances on the LC circuit are inherently minimized. This is in distinction to certain of the prior art circuits in which the active element of the LC circuit does saturate, tending to make detection of output sensor signals less stable, less uniform in response, or more complicated.

Because the output of the circuit which senses induced resistance is insensitive to the effects of induced reactance, the output is more sensitive to the presence of cracks in metal objects in proximity with the probe of the circuit. Moreover, the output is not controlled by the magnetic properties of the metal objects in proximity with the probe, thus allowing use of aluminum or iron or other metals without substantial change of sensitivity of the circuit. In typical circuits of the prior art, a change in the overall inductance or capacitance in the system effects frequency of oscillation as well as the amplitude of oscillation and the detector of the oscillation is frequency sensitive.

Consequently, when a ball comes into proximity with the probe of the circuit, the only reflected effect appearing at the output of the sensing circuit is the change in resistance induced into the circuit. This characteristic presents several advantages.

One advantage is in crack detection. The crack detector of the present invention uses filter circuitry to detect changes in the output signals that occur at the same frequency at which a metal object in proximity with a probe is rotating. Cracks in the metal object affect the overall induced resistance more significantly than the induced reactance and can thus be better detected in this manner. If the circuit output were sensitive to induced reactance, then the nearness of the metal object would substantially vary the output and make the effects of the crack less pronounced.

The proximity sensor and metal crack detector of the present invention also has a parts present and probe fault detector circuit. The present invention utilizes a simple circuit with a small number of components. In the detector circuit, the output signal of the sensor circuit biases a transistor. By comparing the voltage effects that occur at the collector and the emitter of this transistor, the detector circuitry can detect the condition of the presence of a metal object in proximity with a probe, and also detect the fault conditions of an electrically open condition in the probe and an electrical short in the probe.

For crack detection the invention has a filter circuit which also samples the output signal of the sensor circuit. By detecting changes in the output signal that occur at the same frequency at which a metal object in proximity with the probe is rotating, this circuit can detect the existence of cracks in the metal object, as such cracks effect the overall induced resistance of the probe.

For applications other than crack detection, the invention provides a reliable and stable circuit suitable for use in limit switch or general proximity indicator applications. The responsiveness to induced resistance and insensitivity to induced reactance allows use with a wider variety of metals in many applications.

BRIEF DESCRIPTION OF THE DIAGRAMS

FIGS. 2-5 are schematic diagrams of various circuits of the present invention that are shown in FIG. 1.

DESCRIPTION OF THE PREFERRED EMBODIMENT

Figure 1:
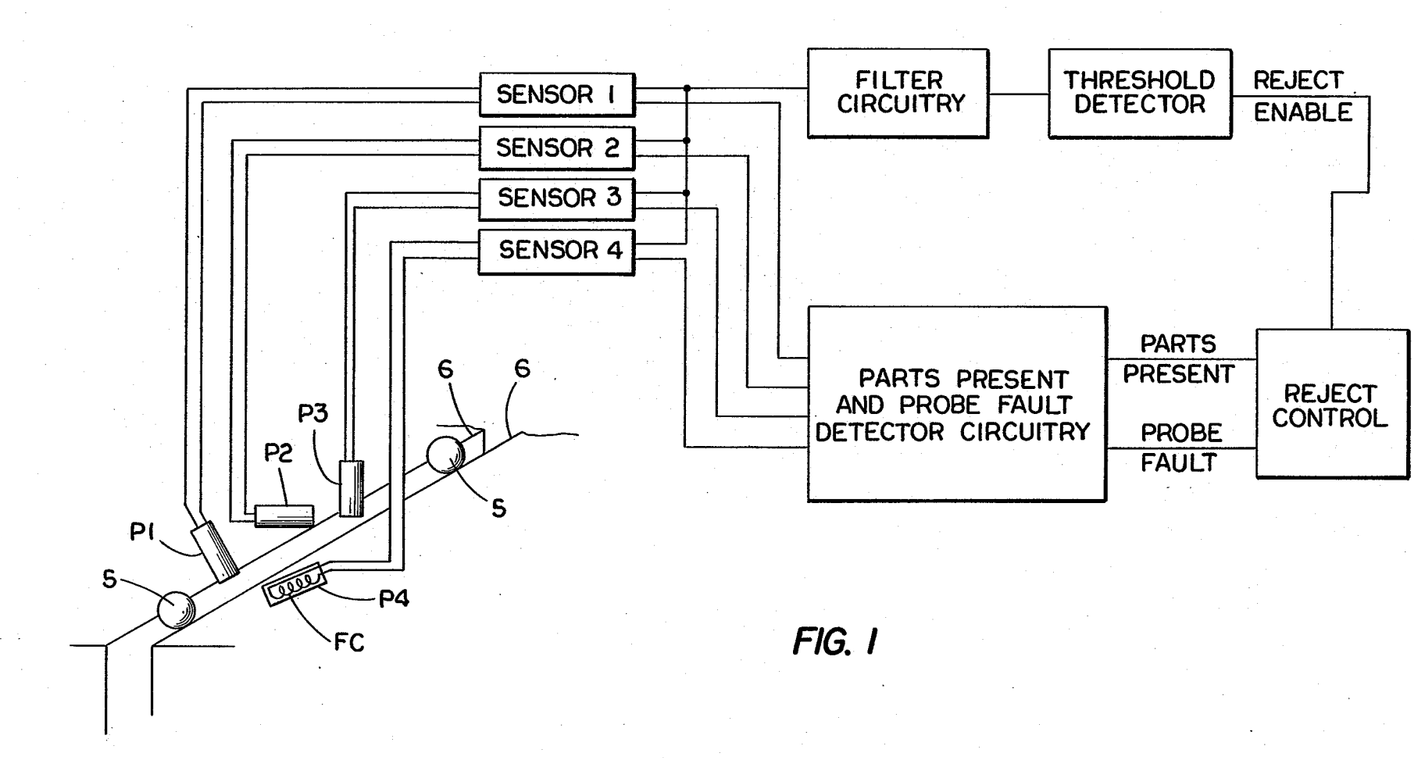
FIG. 1 is a block diagram showing the various circuits of the present invention and indicating the manner in which they are interconnected.

FIG. 1 illustrates the general manner in which the preferred embodiment operates. A metal ball 5 is rolled along an incline on two uniformly spaced-apart guides past four probes P1-4. The guides 6 are spaced apart a distance slightly smaller than the diameter of the metal ball 5. This causes the ball to roll at a high rate of rotation even though its linear motion is relatively slow.

Each of probes P1-4 contains a coil FC and is inductively coupled to sensor 1-4 respectively. Sensors 1-4 each have LC oscillation circuitry designed in the same manner, except the capacitor component values are chosen so that the circuitry oscillates at different, non-harmonic, frequencies in each sensor. Sensors 1-4 each have outputs to the parts present and probe fault detector circuitry and to the filter circuitry. The filter circuitry is broadly tuned to the rotation rate of the ball. The filter circuitry filters out undesired frequencies and produces a signal which is indicative of the existence of a crack in the metallic ball 5. Threshold detector produces a reject enable signal if the output of filter circuitry is sufficient to indicate that a crack does exist in ball 5.

Parts present and probe fault detector circuitry produces a parts present signal when a ball 5 comes into proximity with one of probes P1-4; and produces a probe fault signal if one of probes P1-4 is malfunctioning due to either an open or shorted circuit.

Reject control receives the reject enable, parts present, and probe fault signals, and controls the rejection of cracked balls and the continued operation of the system.

Figure 2:
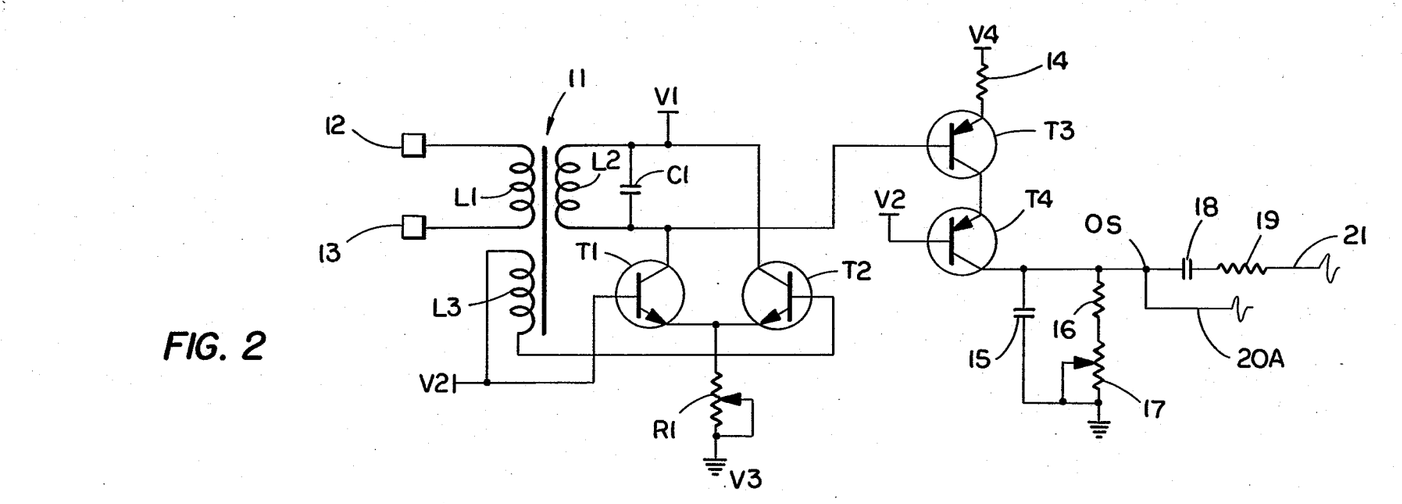
FIG. 2 is a schematic diagram of one of the four sensor circuits.

The circuit of sensor 1 is illustrated in FIG. 2 and is described as follows.

In the preferred embodiment, a capacitor C1 is connected across the ends of an inductor L2 to form an LC resonator. Inductor L2 is one of three windings of a high Q pulse transformer 11. The transformer 11 couples the inductor L2 of the resonator with winding L1, and with winding L3. Terminals 12 and 13 are located at the ends of winding L1 and are used to connect with probe P1.

The base of transistor T2 connects directly to one end of winding L3. The base of transistor T1 connects to voltage terminal V2 and to the other end of winding L3. In the preferred embodiment voltage terminal V2 provides a constant voltage of about 5 volts. The collector of transistor T1 connects directly to one end of winding L2. The collector of transistor T2 connects to voltage terminal V1 and to the other end of winding L2. In the preferred embodiment the voltage source that is supplied is 11.3 volts. The emitters of transistors T1 and T2 are connected directly to each other. Variable resistor R1 connects between third voltage terminal V3 and the emitters of transistors T1 and T2. The third voltage terminal V3 is electrical ground. Transistors T1 and T2 are NPN junction type transistors.

The base of a third transistor T3 is connected to the collector of transistor T1. Resistor 14 connects between the emitter of transistor T3 and a fourth voltage terminal V4. In the preferred embodiment, voltage terminal V4 provides a voltage source of about 12 volts. It is preferable that voltage terminal V4 has a higher voltage than voltage terminal V1 by approximately the voltage differential across the emitter base junction of transistor T3. The collector of transistor T3 connects to the emitter of transistor T4. The base of transistor T4 connects to voltage terminal V2 and the collector of transistor T4 is the electrical point OS. Transistors T3 and T4 are PNP junction type transistors.

Capacitor 15 in parallel with the series connection of resistor 16 and variable resistor 17 connect between the electrical point OS and ground. Capacitor 18 and resistor 19 are in series between electrical point OS and line 21. Line 21 connects the sensor circuit of FIG. 2 with the filter circuit and threshold detector of FIG. 3. Sensors 2-4 are configured and connected in the same manner, except that the values of capacitor C1 are chosen so that each of the sensors 1-4 oscillate at different, non-harmonic frequencies.

Figure 3:
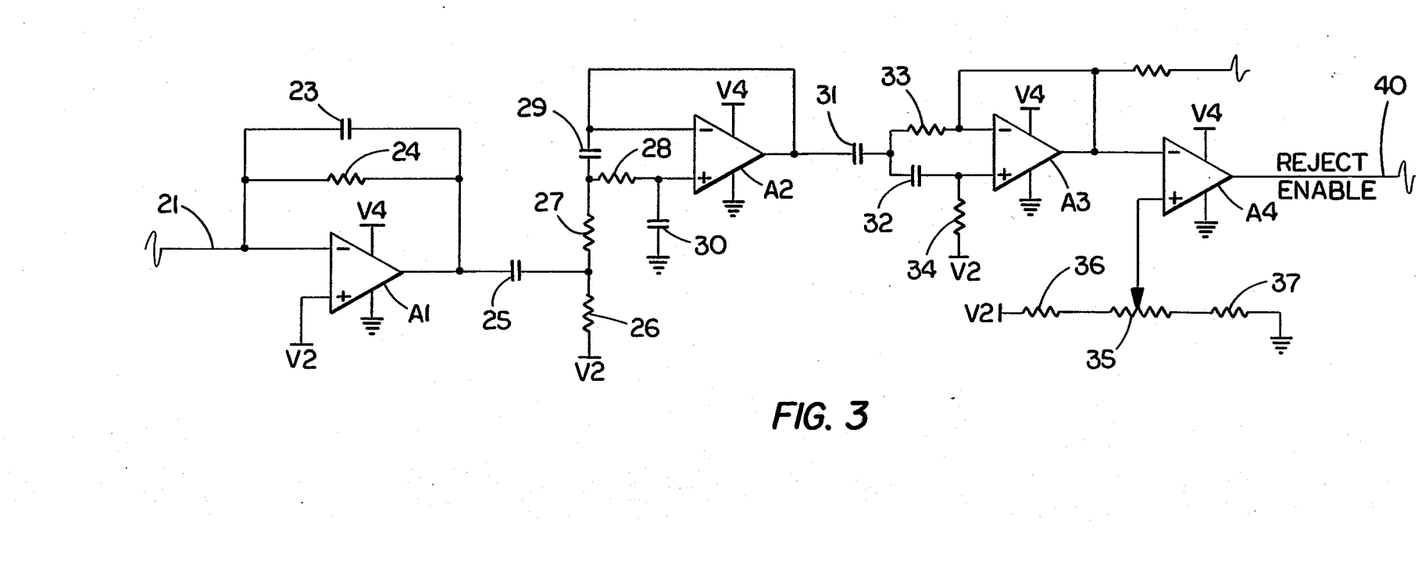
FIG. 3 is a schematic diagram of the filter circuit and the threshold detector.

Referring to the filter circuitry and threshold detector shown in FIG. 3, voltage terminal V2 is connected to the non-inverting input of amplifier A1. Capacitor 23 and resistor 24, in parallel connect between the inverting input and the output of amplifier A1. A line 21 coming from each of sensors 1-4 connects directly to the inverting input of amplifier A1.

The output of amplifier A1 is connected through the series combination of capacitor 25, resistor 27 and resistor 28 to the non-inverting input of amplifier A2. Resistor 26, connects between voltage terminal V2 and the junction of capacitor 25 and resistor 27. Capacitor 29 connects between the inverting input of amplifier A2 and the junction of resistors 27 and 28. Capacitor 30 connects between the non-inverting input of amplifier A2 and ground. The output of amplifier A2 connects directly to the input of amplifier A2.

The output of amplifier A2 is coupled to the non-inverting input of amplifier A3 through the series combination of capacitors 31 and 32. Resistor 33 connects between the inverting input of amplifier A3 and the junction of capacitors 31 and 32. Resistor 34 connects between the non-inverting input of amplifier A3 and voltage terminal V2. The output of amplifier A3 connects directly to the input of amplifier A3.

The output of amplifier A3 also connects to the inverting input of amplifier A4. The series combination of resistor 36, potentiometer 35 and resistor 37 provide a voltage divider by the combination's connection between voltage terminal V2 and ground. The non-inverting input of amplifier A4 connects to a selectable threshold voltage at the variable "wiper" point of potentiometer 35. The output of amplifier A4 is line 40 which connects between FIG. 3 and FIG. 5.

Figure 4:
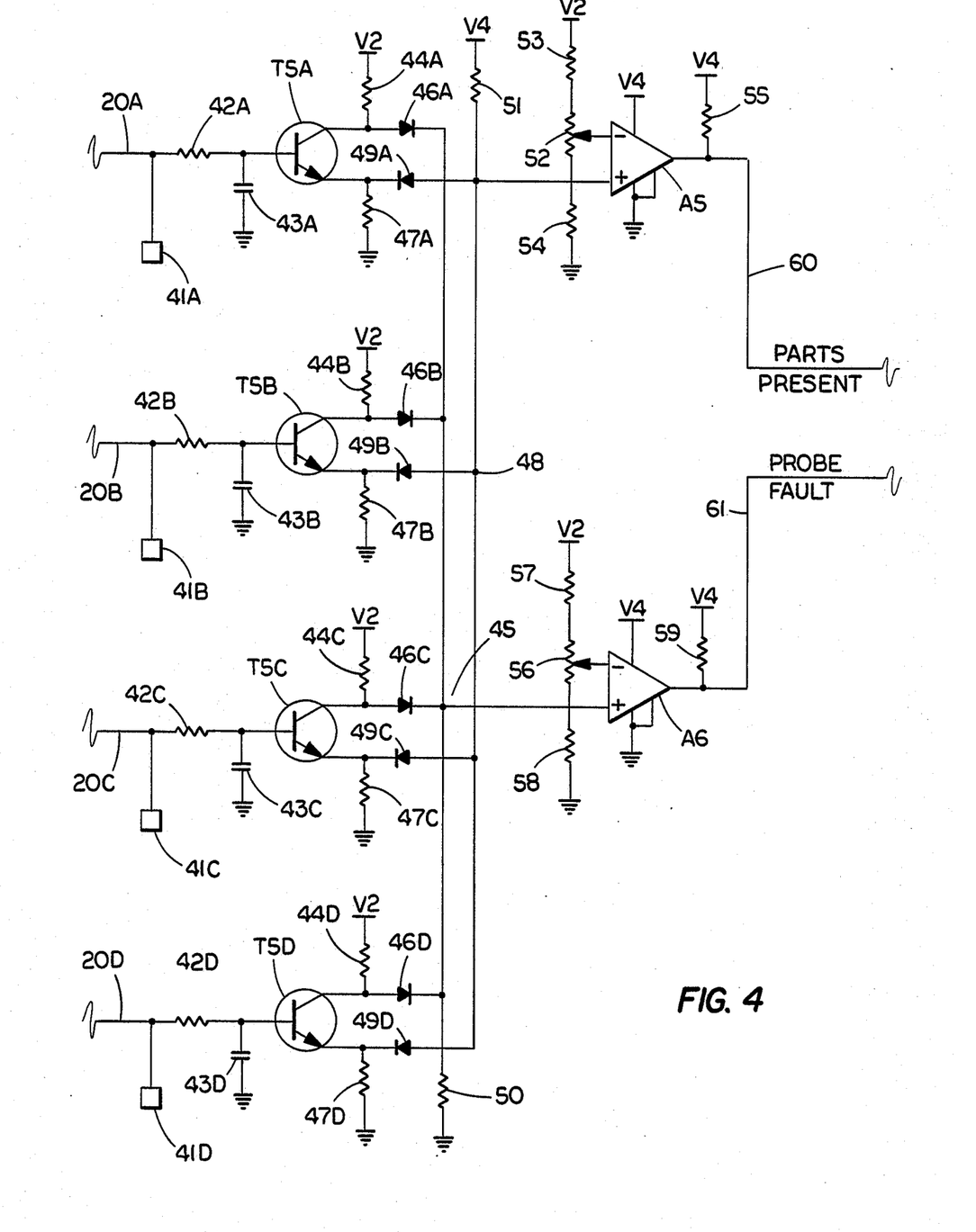
FIG. 4 is a schematic diagram of the parts present and probe fault detector circuit.

Referring to the parts present and probe fault detector circuitry of FIG. 4, line 20A connects sensor 1 of FIG. 2 with this circuitry. Lines 20B-D of FIG. 4 are connected to corresponding points of sensors 2, 3 and 4 respectively to which line 20A connects to sensor 1 in FIG. 2.

Lines 20A-D connect with terminal points 41A-D respectively; and connect to the bases of transistors T5A-D through resistors 42A-D (10,000 ohms) respectively. Terminal points 41A-D are tests points which can be used to check output signals of sensors 1-4. Transistors T5A-D are NPN junction type transistors. Capacitors 43A-D connect between ground and the bases of transistors T5A-D respectively. The collectors of transistors T5A-D connect to voltage terminal V2 through resistors 44A-D (100,000 ohms) and to the electrical point 45 through diodes 46A-D respectively; the cathodes of diodes 46A-D being connected directly to electrical point 45. The emitters of transistors T5A-D are connected to ground through resistors 47A-D (100,000 ohms) respectively; and are connected to the electrical point 48 through diodes 49A-D respectively; the anodes of diodes 49A-D being directly connected to electrical point 48. Resistor 50 (1 megohm) connects between electrical point 45 and ground. Electrical point 45 connects to the non-inverting input of amplifier A6. Resistor 51 (1 megohm) connects between electrical point 48 and voltage terminal V4. Voltage terminal V4 connects to the non-inverting input of amplifier A5.

The series combination of resistor 53, potentiometer 52 and resistor 54 provide a voltage divider by the combination's connection between voltage terminal V2 and ground. The inverting input of amplifier A5 connects to a selectable threshold voltage at the variable "wiper" point of potentiometer 52. Resistor 55 connects between the output of amplifier A5 and voltage terminal V4. The output of amplifier A5 provides a parts present signal on line 60.

The series combination of resistor 57, potentiometer 56 and resistor 58 provide a voltage divider by the combination's connection between voltage terminal V2 and ground. The inverting input of amplifier A6 connects to a selectable threshold voltage at the variable "wiper" point of potentiometer 56. Resistor 59 connects between the output of amplifier A6 and voltage terminal V4. The output of amplifier A6 provides a probe fault signal on line 61. Amplifiers A1-6 all use voltage terminal V4 as a voltage supply and are referenced to ground (V3). Line 60 and 61 connect between FIG. 4 and FIG. 5.

Figure 5:
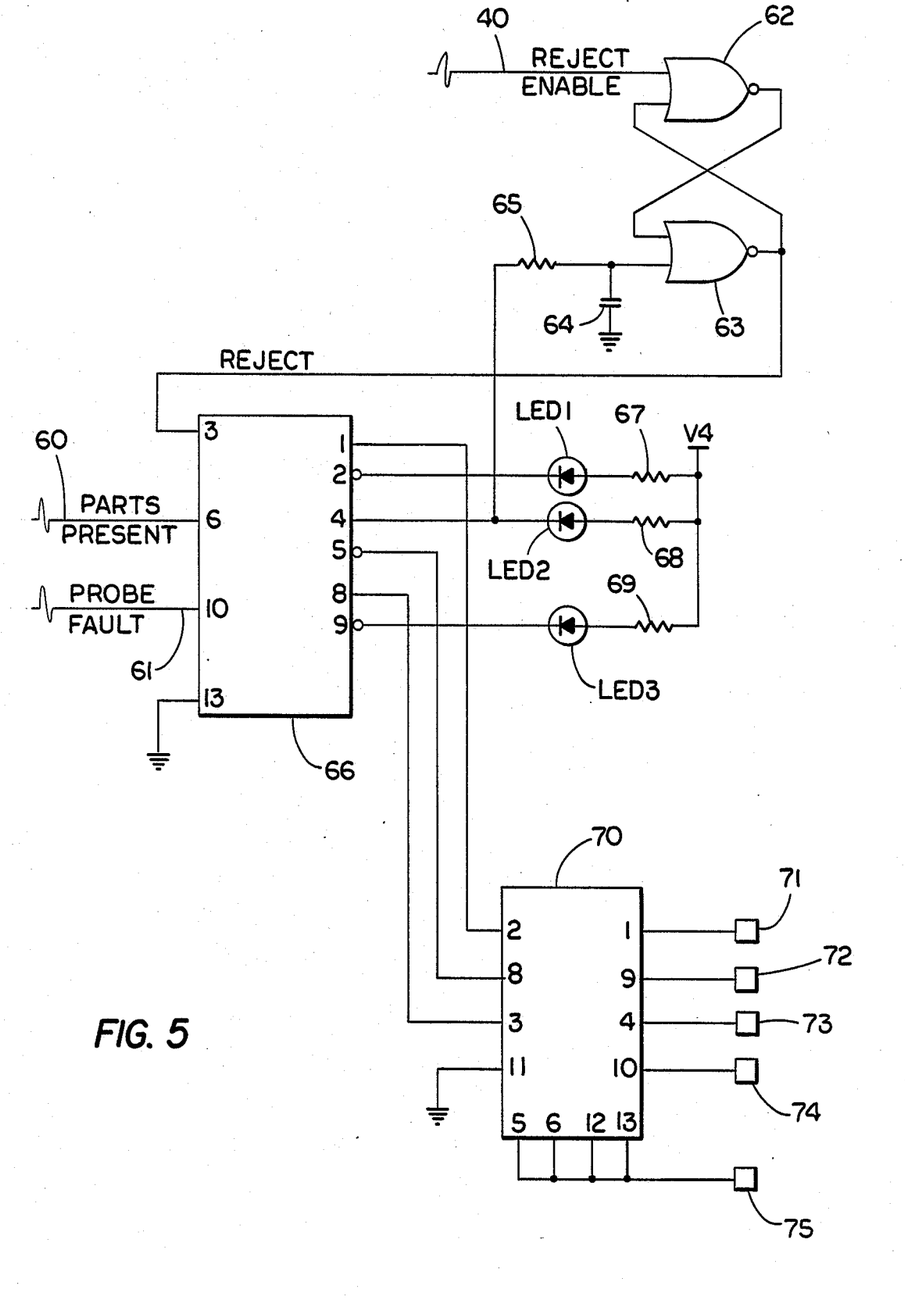
FIG. 5 is a schematic diagram of the reject control.

Referring to the reject control of FIG. 5, line 40 connects to one of the input terminals of the NOR gate 62. The other input of NOR gate 62 connects to the output of NOR gate 63. The output of NOR gate 62 connects to one of the inputs of NOR gate 63. A resistor 65 connects the other input of NOR gate 63 to terminal 4 of integrated circuit 66. A capacitor 64 connects between ground and the juncture of resistor 65 and NOR gate 63.

Integrated circuit 66 provides inverted and non-inverted buffered outputs of the parts present, probe fault and reject signals. The integrated circuit used in the preferred embodiment is model number 4041. Terminal 3 of integrated circuit 66 is an input which is connected to the reject signal from the output of NOR gate 63. Terminals 1 and 2 are the corresponding non-inverted and inverted outputs respectively of the reject signal connected to terminal 3. Terminal 6 of integrated circuit 66 is connected to line 60. Terminals 4 and 5 are the corresponding non-inverted and inverted outputs respectively of the parts present signal connected to terminal 6. Terminal 10 of integrated circuit 66 is connected to line 61. Terminals 8 and 9 are the corresponding non-inverted and inverted outputs respectively of the probe fault signal connected to terminal 10. Light emitting diode LED1 and resistor 67 in series connect between terminal 2 of integrated circuit 66 and voltage terminal V4. Light emitting diode LED2 and resistor 68 in series connect between terminal 4 of integrated circuit 66 and voltage terminal V4. Light emitting diode LED3 and resistor 69 in series connect between terminal 9 of integrated circuit 66 and voltage terminal V4. The anodes of light emitting diodes LED1, LED2 and LED3 are connected to the resistors 67, 68 and 69 respectively.

Integrated circuit 70 is an output signal control device (transmission gate) which can be utilized to periodically apply the outputs of the reject control circuit to a common data bus used with other circuitry. The device used in the preferred embodiment is part number MC14016 made by Motorola Semiconductors, Phoenix, Az. Output terminals 1, 5 and 8 of integrated circuit 66 are connected to input terminals 2, 8 and 3 of integrated circuit 70, respectively. Input terminal 11 of integrated circuit 70 is connected to ground. Output terminals 1, 9, 4 and 10 of integrated circuit 70 connects with common data bus terminals 71, 72, 73 and 74 respectively. Control terminals 5, 6, 12 and 13 connect with an output enable signal at terminal 75.

The preferred embodiment of the present invention is particularly useful in the detection of cracks in metal ball bearings. In the preferred embodiment a metal ball is rotated at a specified frequency of about 60 cycles per second. This rotation is accomplished by rolling the metal ball between two uniformly spaced apart guides 6 that are positioned at an incline. In this manner metal balls are rolled past probes P1-4 at a rate of about 2 per second.

Each of the probes P1-4 contains a ferrite coil FC. Probe P1 is inductively coupled to sensor 1 through transformer 11. Probes P2-4 are inductively coupled to sensors 2-4 respectively, in the same fashion.

As has been previously stated, the present invention is primarily responsive only to resulting changes in induced resistance and is relatively insensitive to changes in induced inductance. When a metal object comes into proximity with one of the probes P1-4, the amplitude of oscillation of the corresponding sensor 1-4 is affected and detected, but the frequency of oscillation does not affect the detected signal.

Each of sensors 1-4 is selected to resonate at a different frequency between 0.1 and 2 MHz. Non-harmonic frequencies are chosen in order to avoid interference between the sensors. Frequencies in the order of 1 MHz are chosen in the preferred embodiment because they provide a good coupling to detect induced resistance, are sufficiently low to minimize problems with cable lengths and radiation, and are sufficiently high to avoid an interference problem in the filter circuitry used to detect the ball rotation frequency.

Transistors T3 and T4 detect the amplitude of oscillation of sensor 1 and produce a signal at electrical point OS which varies from ground to 5 volts, depending upon the amplitude. It there is no oscillation (probe P1 has a short), then transistors T3 and T4 remain off and the output at electrical point OS is ground. If the resistance in the circuit is infinite (electrically open condition in probe P1) then oscillation of sensor 1 is at a maximum and a maximum signal of 5 volts at electrical point OS.

When probe P1 is functioning properly, and there is no metal object in proximity with probe P1, then the internal resistance causes the amplitude of oscillation to be somewhat less than maximum. The output at OS therefore is between ground and 5 volts. This normal oscillation output at OS may be adjusted by adjusting the settings of variable resistors R1 and 17.

If a metallic ball then comes into proximity with probe P2 eddy currents within the metallic ball are induced. The resulting overall decrease in resistance appearing across the LC resonator results in a reduction in the amplitude of oscillation and a corresponding reduction in the output voltage at electrical point OS.

The existence of a crack within the metallic ball, however, inhibits the induction of eddy currents within the ball. Therefore the decrease in the amplitude of oscillation and corresponding output is not as great as it would be without a crack.

There are three frequency components of the oscillation of transistors T1 and T2. They are (1) the 0.1 to 2 MHz frequency of the LC resonator, (2) the 2 Hz fluctuation which occurs as each ball rolls past probe P1, and (3) intermediate fluctuations that occur at about 60 Hz as a result of the varying proximity of a crack to probe P1 as the ball rotates in proximity with probe P1.

Components 15-21 of FIG. 2 and the filter circuitry of FIG. 3 (amplifiers A1, A2, and A3 and their related components) filter out the high frequency of the oscillator and the low cycle frequency of the passing balls. The remaining 60 Hz signals at the output of amplifier A3, if sufficiently high in amplitude in relation to the threshold setting of potentiometer 35, will produce 60 Hz pulses at the output of amplifier A4. These pulses are reflective of the existence of a crack within the ball being tested.

Referring to the parts present and probe fault detector circuitry of FIG. 4, common circuitry detects both the conditions of a part being in proximity with one of the probes P1-4 and of a fault condition (open or short) existing in any one of the probes P1-4.

As previously mentioned, the output to line 20A varies from ground to 5 volts. During normal oscillation (no probe fault, no part present) the output is about 3 volts. This signal is applied to the base of transistor T5A. If the output signal applied to the base of transistor T5A goes to ground (short in probe P1) then transistor T5A turns off and the voltage at the collector goes high, indicating the fault condition. On the other hand, if the output signal goes to 5 volts (electrically open condition in probe P1) the transistor T5A saturates, resulting a logic high output at its collector. In either case, the logic high output of any one of the transistors T5A-D is detected by amplifier A6 which produces a probe fault condition signal through line 61. The sensitivity of probe fault detection can be selected by adjusting the setting of the variable point of potentiometer 56.

The same transistor T5A also is used in a circuit to detect a part being present (the existence of a metallic object in proximity with probe P1).

Because the existence of a metallic ball reduces the voltage output at electrical point OS, the output at the emitter of transistor T5A is also reduced. This reduction is sensed by amplifier A5 through diode 49A and electrical point 48. Amplifier A5 responds by providing a parts present signal through line 66 when any one of transistors T5A-D has a sufficiently low output. The sensitivity of parts present detection can be selected by adjusting the reference voltage from the variable point 55 of potentiometer 52. Amplifier A5 serves as a comparator between the voltage at electrical point 48 and the voltage from potentiometer 52.

As illustrated in FIG. 5, NOR gates 62 and 63 form a flip-flop configuration which produces a reject output signal when both a parts present signal and a reject enable signal are present. The reject output signal together with the parts present signal (line 60) and probe fault signal (line 61) are inputted into integrated circuit 66, which provides corresponding buffered inverted and non-inverted outputs for the transmission gates of integrated circuits 70, for the input to NOR gate 62 and for the operation of the reject indicator light LED 1, the parts present indicator light LED 2, and the probe fault indicator light LED 3.

In operation of the preferred embodiment of the method of the present invention, a metallic ball is rolled at a rate of 60 revolutions per minute down an incline between two uniformly spaced guides as shown in FIG. 1. The metallic ball rolls past probes P1, P2, P3, and P4. Each probe is aligned differently with respect to the rolling ball in order that any cracks which exist will pass close to at least one probe. Sensors 1, 2, 3, 4 having LC oscillations of 1 MHz, 1.3 MHz, 1.7 MHz and 1.9 MHz respectively, each individually responds to the proximity of the ball with their corresponding probes P1, P2, P3, and P4, by diminishing in the amplitude of oscillation. This decrease in amplitude of oscillation is caused by the electronic circuit's responsiveness to induced resistance in the coils of probes P1-4.

The balls roll past the probes at a rate of approximately 2 balls/second. When in proximity to the probes, the balls are rotating at a frequency of approximately 60 Hz, thereby producing a 60 Hz component to the extent of any anomalies in the induced resistance due to nonuniformities in the balls, such as a crack on the surface.

Each sensor 1-4 has a normal output voltage of 3 volts D.C. component. When the D.C. output of one or more of the sensors 1-4 diminishes to less than 2 volts, then detector circuitry produces a parts present signal. The low frequency A.C. component at OS is combined from all sensors 1-4 and sent to filter circuitry which filters out the high frequency of LC oscillation and the low frequency of the passing balls and produces a signal when an oscillation is detected of the same frequency as that of rotation of the balls.

Additionally, when output voltage of one of sensors 1-4 drops below 1.0 volts (indicating a short in a corresponding probe) or if the voltage output of one of sensors 1-4 increases above 4.0 volts (indicating an electrically open condition in a corresponding probe) then probe fault detector circuitry produces a signal, indicating that one of probes P1-4 is malfunctioning.

Numerous alterations in the present invention are contemplated which are considered to be within the scope of the invention. For instance, the number of probes and frequencies of oscillation may be varied. Also, the particular arrangement of components in the LC oscillators may be varied, yet maintain the general purpose of the circuit. Or the particular means of detection and reject control may be accomplished in a different manner. While there is disclosed herein the preferred embodiment in the form of a crack detector for ball bearings, it is contemplated that the sensor circuit alone or in combination with other circuits can be used generally for proximity detection applications and limit switch applications.

While there has been described above the principles of this invention in connection with specific apparatus, it is to be clearly understood that this description is made only by way of example and not as a limitation to the scope of the invention.

What is claimed is:

1. A proximity sensor circuit comprising:
   (a) a transformer containing first, second, and third mutually inductively coupled windings, each having a first and second end,
   (b) a probe including a coil connected across said first winding,
   (c) a capacitor connected across said second winding, the combination forming an LC resonating circuit, (d) first and second transistors each having first, second and third elements, the first element of said first transistor being connected to the first end of said second winding, and the second element of said second transistor being connected to the first end of said third winding, (e) a source of voltages having first, second and third terminals providing three different voltage potentials, the first terminal being connected to the second end of said second winding and to the first element of said second transistor, and the second terminal being connected to the second end of said third winding and to the second element of said first transistor, (f) a resistor having a first end connected to the third elements of said transistors, and having a second end connected to the third terminal of said source of voltages.

2. The circuit of claim 1 in which said transistors are NPN type junction transistors and the first, second, and third elements of said transistors are collectors, bases, and emitters respectively.

3. The circuit of claim 1 in which said second and third windings are located on said transformer in such a manner such that a current flowing from the first to the second end of said second winding induces a current that flows from the first to the second end of said third winding.

4. The circuit of claim 1 in which the first terminal of said source of voltages has a voltage potential of about 12 volts, the second terminal of said source of voltages has a voltage potential of about 5 volts, and the third terminal of said source of voltages is ground.

5. The circuit of claim 1 in which said source of voltages additionally has a fourth terminal and the circuit additionally comprises:

(g) a third and a fourth transistor, said transistors being junction transistors, each said transistor having a collector, a base, and an emitter, the collector of said third transistor being connected to the emitter of said fourth transistor, the base of said third transistor being connected to the collector of said first transistor, and the base of said fourth transistor being connected to the second terminal of said source of voltages; and (h) a second resistor having one end connected to the fourth terminal of said source of voltages, and having the other end connected to the emitter of said third transistor.

6. The circuit of claim 5 in which the fourth terminal of said source of voltages has a voltage potential of about 12 volts.

7. The circuit of claim 5 additionally comprising:

(i) filter circuitry means for detecting changes in voltage which occur at a specified frequency which is a lower frequency than the frequency of oscillation of said LC circuit, said filter circuit means being connected to the collector of said fourth transistor.

8. The circuit of claim 5 additionally comprising:

(j) parts present detector circuit means for sampling the voltage at the collector of said fourth transistor and for producing a signal that is in one state when a metal object is in proximity with said probe and in another state when no metal object is in proximity with said probe.

9. The circuit of claim 5 additionally comprising:

(k) probe fault detector circuit means for sampling the voltage at the collector of said fourth transistor and for producing a signal that is in one state when there is an electrical short in said probe and when there is an electrical open condition in said probe and is in another state at all other times.

10. A circuit responsive to induced resistance comprising:

(a) a probe having a coil, and (b) a sensor circuit coupled to said probe, said sensor circuit having an LC resonating circuit and having an output signal that is primarily responsive to the induced resistance into said LC resonating circuit through said probe as opposed to induced reactance through said probe;

(c) a parts present detector means for receiving the output signal from said sensor circuit and for producing a signal that is responsive to induced resistance indicative of the existence of a conductive object in proximity with said probe; and (d) probe fault circuit means for receiving the output signal from said sensor circuit means and for producing a signal responsive to about zero induced resistance indicative of an electrical short circuit in said probe and is responsive to about indefinite induced resistance indicative of an electrical open condition in said probe, said probe fault detector circuit including:

a transistor having a collector, a base, and an emitter, a first resistor connected to the base of said transistor, a source of voltages having first and second terminals providing two different voltage potentials, a second resistor having higher resistance than said first resistor; and having one end connected to the collector of said transistor and the other end connected to the first terminal of said source of voltages, a third resistor having about the same resistance as said second resistor; and having one end connected to the emitter of said transistor and the other end connected to the second terminal of said source of voltages, a comparator having an input voltage point, a reference voltage, and an output voltage, and a fourth resistor having higher resistance than said second and said third resistors; and having one end connected to the input voltage point of said comparator and other end connected to the second terminal of said source of voltages.

11. A circuit responsive to induced resistance comprising:

(a) a probe having a coil, and (b) a sensor circuit coupled to said probe, said sensor circuit having an LC resonating circuit and having an output signal that is primarily responsive to the induced resistance into said LC resonating circuit through said probe as opposed to induced reactance through said probe;

(c) a parts present detector means for receiving the output signal from said sensor circuit and for producing a signal that is responsive to induced resistance indicative of the existence of a conductive object in proximity with said probe; and (d) probe fault circuit means for receiving the output signal from said sensor circuit means and for producing a signal responsive to about zero induced resistance indicative of an electrical short circuit in said probe and is responsive to about indefinite induced resistance indicative of an electrical open condition in said probe, said parts present detector circuit including:

a transistor having a collector, a base, and an emitter, a first resistor connected to the base of said transistor, a source of voltages having first and second terminals providing two different voltage potentials, a second resistor having higher resistance than said first resistor and having one end connected to the collector of said transistor and the other end connected to the first terminal of said source of voltages, a third resistor having about the same resistance as said second resistor; and having one end connected to the emitter of said transistor and the other end connected to the second terminal of said source of voltages, a comparator having an input voltage point, a reference voltage, and an output voltage, and a fourth resistor having higher resistance than said second and said third resistors; and having one end connected to the input voltage point of said comparator and other end connected to the first terminal of said source of voltages.

12. The circuit of claim 11 in which said probe fault detector circuit includes:
   (a) a transistor having a collector, a base, and an emitter,
   (b) a first resistor connected to the base of said transistor,
   (c) a source of voltages having first and second terminals providing two different voltage potentials,
   (d) a second resistor having higher resistance than said first resistor; and having one end connected to the collector of said transistor and the other end connected to the first terminal of said source of voltages,
   (e) a third resistor having about the same resistance as said second resistor; and having one end connected to the emitter of said transistor and the other end connected to the second terminal of said source of voltages,
   (f) a comparator having an input voltage point, a reference voltage, and an output voltage,
   (g) a fourth resistor having higher resistance than said second and said third resistors; and having one end connected to the input voltage point of said comparator and the other end connected to the second terminal of said source of voltages.

13. The circuit of claim 12 in which the transistor of said parts present detector circuit is also the transistor of said probe fault detector circuit.

14. The circuit of claim 13 in which the first resistor, the second resistor, the third resistor and the source of voltages of said parts present detector circuit are also the first resistor, the second resistor, the third resistor and the source of voltages of said probe fault detector circuit.

15. The circuit of claim 14 in which the transistor of said parts present detector circuit and of said probe fault detector circuit is an NPN junction transistor.

16. The circuit of claim 15 in which the first terminal of the source of voltages of said parts present detector circuit and of said probe fault detector circuit has a voltage potential of about 5 volts and the second terminal of the source of voltages of said parts present detector circuit and of said probe fault detector circuit is electrical ground.

17. The circuit of claim 16 in which said specified frequency is about 60 Hz.

* * * * *